United States Patent

Petersen et al.

[11] 3,996,220
[45] Dec. 7, 1976

[54] PRODUCTION OF 4-OXOTETRAHYDRO-1,3,5-OXADIAZINES

[75] Inventors: Harro Petersen, Frankenthal; Klaus Erhardt, Ludwigshafen, both of Germany

[73] Assignee: Badische Anilin- & Soda-Fabrik Aktiengesellschaft, Ludwigshafen (Rhine), Germany

[22] Filed: Oct. 4, 1974

[21] Appl. No.: 512,217

Related U.S. Application Data

[63] Continuation of Ser. No. 315,474, Dec. 15, 1972, abandoned.

[30] Foreign Application Priority Data

Dec. 22, 1971 Germany .......................... 2163854

[52] U.S. Cl. ............................................ 260/244 R
[51] Int. Cl.² ...................................... C07D 273/04
[58] Field of Search ..................................... 260/244

[56] References Cited

OTHER PUBLICATIONS

Houben–Weyl, Methoden der Organiochem Chemie, vol. 14/2, pp. 327–328, 348 (1963).

*Primary Examiner*—Henry R. Jiles
*Assistant Examiner*—R. W. Ramsuer
*Attorney, Agent, or Firm*—Johnston, Keil, Thompson & Shurtleff

[57] ABSTRACT

The production of 4-oxotetrahydro-1,3,5-oxadiazines by reaction of urea (which may be methylolated) with formaldehyde in specific molar proportions and under specific conditions of temperature and pH for not more than thirty minutes. The products are textile finishing agents and valuable starting materials for the production of textile finishing agents, particularly for cellulosic textiles.

7 Claims, No Drawings

PRODUCTION OF 4-OXOTETRAHYDRO-1,3,5-OXADIAZINES

This is a continuation of application Ser. No. 315,474, filed Dec. 15, 1972, now abandoned.

The invention relates to a process for the production of 4-oxotetrahydro-1,3,5-oxadiazines by reaction of urea or methylolated urea with formaldehyde in specific molar ratios and under specific conditions of temperature and pH for not more than thirty minutes.

Methods for the production of 3,5-bis-(alkoxymethyl)-4-oxo-1,3,5-oxadiazines (3,5-bisalkoxymethylurones) are already known. Thus Bull. Chem. Soc. Japan, Volume 11 (1936), page 259 discloses a method in which in a first stage a mixture of 1 mole of urea and 4 moles of formaldehyde is reacted in the presence of barium hydroxide at refluxing temperature, then the reaction mixture is concentrated and in a second stage at room temperature is reacted with methanol in the presence of hydrochloric acid to form 3,5-bis(methoxymethyl)-4-oxo-1,3,5-oxadiazine (N,N'-dimethylolurone dimethyl ether). An article in J. Org. Chem., Volume 28 (1963), pages 1876 and 1877 discloses that the two methoxymethyl groups are eliminated from such an oxadiazine in an acid aqueous medium at boiling temperature so that the parent substance, known as urone, is obtained. According to the method described in German Printed Application (DAS) No. 1,123,334 3,5-bis-(alkoxymethyl)-4-oxotetrahydro-1,3,5-oxadiazines may be prepared by a two stage method in which in stage (1) 1 mole of urea is reacted with more than five moles of formaldehyde at a temperature of from 40° to 80° C and at a pH above 10 and after the reaction mixture obtained has been concentrated it is reacted in stage (2) with an alcohol in the presence of an acid. As may be seen from the description and the Examples the reaction is carried out in stage (2) at room temperature.

All these methods of manufacture have disadvantages when used on an industrial scale. Thus considerable amounts of alkali or base used in the first stage and the acid used in the second stage have to be neutralized and separation of the salts is expensive. Moreover in the first stage of this method, by reason of a Cannizzaro reaction, formates are formed from formaldehyde in the presence of a base and in many cases this limits the use of the end product (unless a special purification is carried out) because of the reducing effect of the formates.

It is also disclosed in Houben-Weyl, "Methoden der organischen Chemie", volume XIV/2, pages 327 et seq. and 348 that when 1 mole of urea is heated to above 80° C with more than 4.5 moles of formaldehyde at a pH lower than 3 it reacts to form water-soluble polycondensation products which are highly viscous and water-clear.

It is an object of this invention to provide a new process for producing methylolated 4-oxotetrahydro-1,3,5-oxadiazines in a simpler and more economical manner.

We have found that a methylolated 4-oxotetrahydro-1,3,5-oxadiazine of the general formula (I):

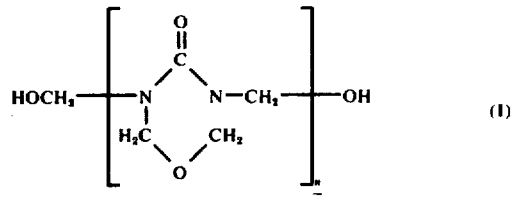

in which $n$ is 1, 2 or 3 is obtained advantageously by reacting a urea of the general formula (II):

in which the individual radicals R are identical or different and each is hydrogen or the radical HOCH$_2$— at a pH of not more than 2.5 and a temperature of from 80° to 110° C for a period of not more than thirty minutes with formaldehyde in a molar ratio of (4 minus $x$) moles of formaldehyde per mole of urea, $x$ being the number of methylol groups attached to the nitrogen atom of starting material (II).

When urea is used as the starting material, the reaction may be represented by the following formulae:

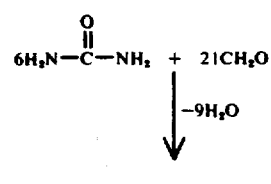

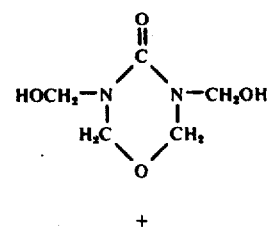

+

-continued

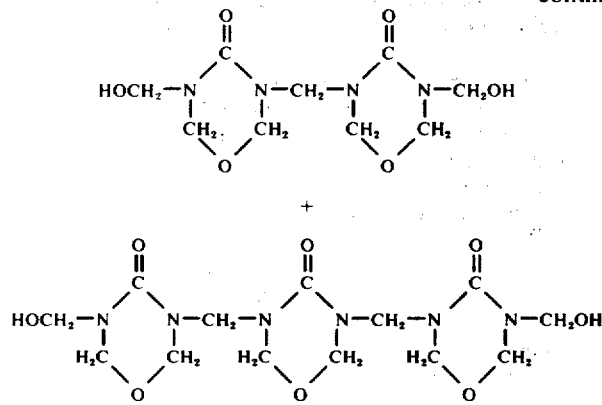

The invention is based on the observation that surprisingly the abovementioned end products (I) form in a high yield in the first thirty minutes of the reaction of urea of methylolated urea with formaldehyde under specific conditions as regards molar ratio, temperature and pH. As compared with the said methods the process of the invention gives methylolated 4-oxotetrahydro-1,3,5-oxadiazines in better yields and purity and is easier to carry out and more economical. Polycondensations do not take place to any appreciable extent.

Urea, N-methylolurea, N,N'-dimethylolurea and N,N,N'-trimethylolurea are used as starting material (II). The reaction mixture containing the said ureas (II) obtained in the reaction of urea with formaldehyde may also be used instead of the said methylolureas (II). Thus for example a reaction mixture which generally contains from 5 to 10% by weight of monomethylolurea, from 40 to 60% by weight of dimethylolurea and from 10 to 30% by weight of trimethylolurea is obtained in the reaction of 1 mole of urea with from 4 to 5 moles of formaldehyde at from 50° to 80° C at pH from 5 to 7.5 during from thirty to ninety minutes. Mixtures of starting materials (II) are also suitable. The end products obtained are as a rule mixtures of the three end substances (I) with $n$ equal to 1, 2 and 3. The proportions of these end substances (I) in such mixtures are generally from 50 to 80%, preferably from 60 to 70%, by weight of end substance (I) with $n$ equal to 1 (urone), from 15 to 30% by weight of end substance (I) with $n$ equal to 2 (methylenebisurone) and from 5 to 20% by weight of end substance (I) with $n$ equal to 3 (bismethylenetrisurone). The proportion of urone is greater (and that of bisurone and trisurone less) the larger the amount of formaldehyde used is in relation to starting material (II).

Formaldehyde is another starting material in the process; this is conveniently used as an aqueous solution which may be stabilized with alcohol. It may also be used in the form of paraformaldehyde. At least 4 minus $x$, advantageously from 4 minus $x$ to 10 minus $x$, moles of formaldehyde is used per mole of urea in the reaction. The reaction is preferably carried out with from 4 to 6 moles of formaldehyde per mole of unsubstituted urea (II) ($x$ equal to zero), with from 3 to 5 moles of formaldehyde per mole of monomethylolated urea (II) ($x$ equal to 1), from 2 to 4 moles of formaldehyde per mole of dimethylolated urea (II) ($x$ equal to 2) and from 1 to 3 moles of formaldehyde per mole of trimethylolated urea (II) ($x$ equal to 3).

The reaction is carried out at a pH of not more than 2.5, preferably at from 0.5 to 2.0. The appropriate pH is conveniently set up by adding an inorganic or organic acid which does not oxidize under the reaction conditions. Examples of such acids are phthalic acid, oxalic acid; sulfonic acids such as p-toluenesulfonic acid; sulfuric acid, phosphoric acid or hydrogen chloride, for example in the form of hydrochloric acid. The acid is generally added in an amount of from 0.1 to 5% by weight based on the weight of starting material (II).

The reaction is carried out at a temperature of from 80° to 110° C, preferably from 90° to 100° C, at atmospheric or superatmospheric pressure, continuously or batchwise. Water is generally used as the reaction medium, for example in the form of an aqueous, for example 35 to 40% by weight solution of formaldehyde. Reaction periods of not more than thirty minutes, preferably from 0.5 to 15 minutes, particularly from half to five minutes, are used. When the reaction is continued for more than thirty minutes, polycondensation products which are cocondensates of urone rings with urea combined by way of methylene bridges are formed to an increasing extent. The reaction period is advantageously shorter the higher the temperature is and the smaller the pH set up. For example the reaction of urea with 4 moles of formaldehyde at 90° C and a pH of 1 is carried out within only two minutes and at a pH of 2 within fifteen minutes. Reaction periods of from 25 to 30 minutes are advantageous at 80° C and pH 2.5, and reaction periods of half to one minute are advantageous at a temperature of from 100° to 110° C and pH of from 0 to 0.5.

The reaction may be carried out as follows: a mixture of starting material (II), formaldehyde and acid is kept at the reaction temperature for the reaction period at the given pH. A mixture of starting material (II) with formaldehyde may first be heated to the reaction temperature and the acid then added. In a preferred embodiment formaldehyde is mixed with the acid and heated to the requisite temperature; into this solution the urea (II) is then introduced. The reaction mixture is neutralized with caustic soda solution after the reaction and allowed to cool. The mixture of end products (I) is usually further processed immediately and the yield ascertained for example by Raman spectroscopy. The urone ring exhibits a characteristic band at 810 cm$^{-1}$. The end products may also be isolated from the mixture by a conventional method, advantageously by concentration of the mixture, reaction of the residue with an alcohol such as methanol in the presence of an acid, for example hydrochloric acid, neutralization, extraction with a suitable solvent such as chloroform and separation of the end products (I) in the form of bis(methoxymethyl)-urones by distillation at subatmospheric pressure.

Compounds prepared by the process of the invention are textile finishing agents and valuable starting materials for the production of textile finishing agents, particularly for cellulosic textiles. They give crease resist finishes having good resistance to hydrolysis. Thus for example textile cloth may be impregnated therewith in an amount of from 50 to 300 grams per liter of finishing liquor together with formaldehyde or other conventional N-methylol compounds, dried and treated at 80° to 160° C in a condensation unit and thus given a crease resist finish.

The following Examples illustrate the invention. The parts are parts by weight.

EXAMPLE 1 a. Reaction 1500 parts of 40% by weight aqueous formaldehyde solution and 5 parts of 50% by weight sulfuric acid are heated to 90° C. 120 parts of urea is introduced within 5 minutes while stirring. The mixture is then heated for 10 minutes at 90° C. The solution is neutralized with concentrated caustic soda solution and evaporated in vacuo.

b. Characterizing the end products (I) by their bismethyl ethers

The residue which remains is dissolved in 1000 parts of methanol, then 10 parts of concentrated hydrochloric acid is added and the mixture is heated for 3 hours at from 40° to 50° C. The solution is then neutralized with concentrated caustic soda solution, deposited sodium chloride is filtered off and excess methanol is distilled off from the filtrate in vacuo. The residue is extracted with 500 parts of chloroform. After the chloroform has been distilled off, 328 parts of end products (I) are obtained having the composition 75% by weight of N,N'-bismethoxymethylurone having a boiling point of 116° to 118° C at a pressure of 0.5 to 1.5 mm, 20% by weight of N,N'-bismethoxymethyl-(methylenebisurone) having a boiling point of 144° to 159° C at 1 mm and 5% by weight of N,N'-bismethoxymethyl-(bismethylenetrisurone) having a boiling point of 170° to 180° C at 0.5 mm. This is equivalent to a yield of 86% of theory based on urea used.

EXAMPLE 2

10 parts of p-toluenesulfonic acid is added to 900 parts of 40% by weight aqueous formaldehyde solution and heated to 95° C. 120 parts of urea is introduced at 95° C in a period of 5 minutes while stirring. The pH of the reaction mixture is 1.3. The mixture is kept for another 5 minutes at 95° C, then immediately neutralized with 50% by weight caustic soda solution and cooled to room temperature. The contents of end product (I) are determined by Raman spectroscopy and also by way of the bismethyl ethers as described in Example 1. 233 parts of end product (I) of the composition of Example 1 is obtained. This is 75% of theory.

EXAMPLE 3

363 parts of a 70% by weight aqueous methylolation mixture (which in addition to water contains a mixture of dimethylolurea, trimethylolurea and free formaldehyde with a ratio of 4 moles of formaldehyde to 1 mole of urea) is heated to 95° C and, after 5 parts of 50% by weight sulfuric acid has been added, kept at this temperature for five minutes while stirring. The pH is 0.7. The mixture is neutralized with 50% by weight caustic soda solution and cooled to room temperature. The content of end product (I) is determined by Raman spectroscopy and by way of the bismethyl ethers as described in Example 1. 180 parts (65.5% of theory) of end product (I) of the composition of Example 1 is obtained.

EXAMPLE 4

120 parts of dimethylolurea is introduced in the course of 5 minutes into a mixture, heated to 95° C, of 1500 parts of 40% by weight formaldehyde and 5 parts of oxalic acid. The reaction mixture is kept at 90° to 95° C for another 5 minutes, then cooled to room temperature, neutralized with dilute caustic soda solution and filtered. The content of end products (I) is determined by Raman spectroscopy and by way of the bismethyl ethers as described in Example 1. 205 parts of end products (I) of the composition given in Example 1 is obtained. This is 66% of theory.

We claim:

1. A process for the production of a methylolated 4-oxotetrahydro-1,3,5-oxadiazine of the formula (I):

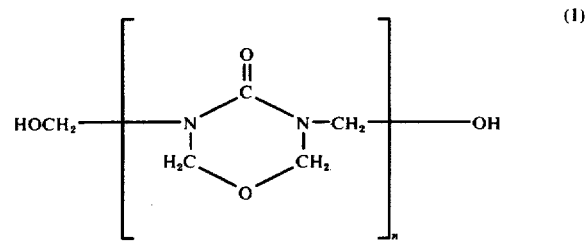

in which $n$ is 1, 2 or 3
wherein
a urea of the formula (II):

in which the individual radicals R are identical or different and each is hydrogen or $HOCH_2$ — is reacted with formaldehyde in a molar ratio of at least 4 minus $x$ moles of formaldehyde per mole of urea, $x$ being the number of methylol groups combined with the nitrogen atoms in starting material (II), at a pH of not more than 2.5 and a temperature of from 80° to 110° C for a period of not more than thirty minutes and there after neutralizing and cooling said reaction mixture.

2. A process as set forth in claim 1 wherein the reaction is carried out, not with the said methylolureas (II), but with a reaction mixture containing these ureas (II) obtained by reaction of urea with formaldehyde at pH from 5 to 7.5.

3. A process as set forth in claim 1 carried out with 4 to 6 moles of formaldehyde per mole of unsubstituted urea (II) ($x$ being zero), 3 to 5 moles of monomethylolated urea (II) ($x$ being 1), 2 to 4 moles of formaldehyde per mole of dimethylolated urea (II) ($x$ being 2) or 1 to 3 moles of formaldehyde per mole of trimethylolated urea (II) (x being 3).

4. A process as set forth in claim 1 carried out at a pH of from 0.5 to 2.0.

5. A process as set forth in claim 1 carried out at a temperature of from 90° to 100° C.

6. A process as set forth in claim 1 carried out with a reaction period of from half a minute to 15 minutes.

7. A process for the production of a methylolated 4-oxotetrahydro-1,3,5-oxadiazine of the formula (I):

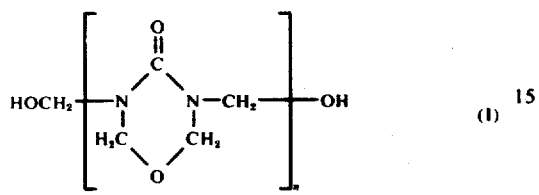

in which $n$ is 1, 2 or 3, wherein
a urea of the formula (II):

in which the individual radicals R are identical or different and each is hydrogen or $HOCH_2-$ is reacted with formaldehyde in a molar ratio of at least 4 minus $x$ moles of formaldehyde per mole of urea, $x$ being the number of methylol groups combined with the nitrogen atoms in starting material (II), at a pH of not more than 2.5 and a temperature of from 80° to 110° C for a period of not more than thirty minutes and thereafter neutralizing the reaction mixture with caustic soda and cooling said reaction mixture.

* * * * *